(12) United States Patent
Gotch

(10) Patent No.: US 8,182,692 B2
(45) Date of Patent: May 22, 2012

(54) SOLUTIONS, DIALYSATES, AND RELATED METHODS

(75) Inventor: Frank A. Gotch, San Francisco, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 614 days.

(21) Appl. No.: 12/128,167

(22) Filed: May 28, 2008

(65) Prior Publication Data

US 2008/0296226 A1    Dec. 4, 2008

Related U.S. Application Data

(60) Provisional application No. 60/940,531, filed on May 29, 2007.

(51) Int. Cl.
*B01D 61/32* (2006.01)
*B01D 61/24* (2006.01)

(52) U.S. Cl. ........ 210/646; 210/645; 210/647; 210/739; 210/745; 210/746; 604/4.01; 422/68.1; 422/82.01; 422/82.02

(58) Field of Classification Search .................. 210/645, 210/646, 647, 739, 745, 746, 85, 103, 134, 210/143; 604/4.01, 28; 422/68.1, 82.01, 422/82.02

See application file for complete search history.

(56) References Cited

U.S. PATENT DOCUMENTS

| | | | |
|---|---|---|---|
| 1,406,372 A | 2/1922 | Grapp | |
| 1,689,432 A | 10/1928 | Hartwig | |
| 2,107,173 A | 2/1938 | Bauer | |
| 3,130,289 A | 4/1964 | Katzman et al. | |
| 3,605,783 A | 9/1971 | Pecker et al. | |
| 3,694,625 A | 9/1972 | Cole | |
| 3,808,401 A | 4/1974 | Wright et al. | |
| 4,136,708 A | 1/1979 | Cosentino et al. | |
| 4,508,622 A | 4/1985 | Polaschegg et al. | |
| 4,676,467 A | 6/1987 | Palsulich | |
| 4,778,451 A | 10/1988 | Kamen | |
| 4,808,161 A | 2/1989 | Kamen | |
| 4,826,482 A | 5/1989 | Kamen | |
| 4,869,286 A | 9/1989 | Williams et al. | |
| 4,902,282 A | 2/1990 | Bellotti et al. | |
| 4,902,877 A | 2/1990 | Grasso et al. | |
| 4,950,134 A | 8/1990 | Bailey et al. | |

(Continued)

FOREIGN PATENT DOCUMENTS

EP        0311848        4/1989

(Continued)

OTHER PUBLICATIONS

Gambro®, "Prismaflex™ anticipating critical care needs and taking our innovative response . . . to new heights," © 2004, Gambro Inc., Lakewood, CO, 8 pp.

(Continued)

*Primary Examiner* — John Kim
(74) *Attorney, Agent, or Firm* — Fish & Richardson P.C.

(57) ABSTRACT

Solutions, dialysates, and methods for measuring solutes in blood and/or for treating blood. In one aspect of the invention, a method of performing dialysis includes placing a solution in communication with blood of a subject, where a concentration of at least one electrically conductive solute in the solution, prior to being placed in communication with the blood of the subject, is substantially equal to a concentration of the at least one electrically conductive solute in the blood of the subject.

26 Claims, 4 Drawing Sheets

U.S. PATENT DOCUMENTS

| | | | |
|---|---|---|---|
| 4,976,162 A | 12/1990 | Kamen | |
| 5,002,471 A | 3/1991 | Perlov | |
| 5,024,756 A * | 6/1991 | Sternby | 210/93 |
| 5,088,515 A | 2/1992 | Kamen | |
| 5,100,554 A | 3/1992 | Polaschegg | |
| 5,116,021 A | 5/1992 | Faust et al. | |
| 5,146,713 A | 9/1992 | Grafius | |
| 5,178,182 A | 1/1993 | Kamen | |
| 5,193,990 A | 3/1993 | Kamen et al. | |
| 5,211,201 A | 5/1993 | Kamen et al. | |
| 5,241,985 A | 9/1993 | Faust et al. | |
| 5,311,899 A | 5/1994 | Isayama et al. | |
| 5,324,422 A | 6/1994 | Colleran et al. | |
| 5,344,392 A | 9/1994 | Senninger et al. | |
| 5,350,357 A | 9/1994 | Kamen et al. | |
| D351,470 S | 10/1994 | Scherer et al. | |
| 5,353,837 A | 10/1994 | Faust | |
| 5,395,351 A | 3/1995 | Munsch | |
| 5,421,208 A | 6/1995 | Packard et al. | |
| 5,421,823 A | 6/1995 | Kamen et al. | |
| 5,431,626 A | 7/1995 | Bryant et al. | |
| 5,438,510 A | 8/1995 | Bryant et al. | |
| 5,447,286 A | 9/1995 | Kamen et al. | |
| 5,474,683 A | 12/1995 | Bryant et al. | |
| 5,486,286 A | 1/1996 | Peterson et al. | |
| 5,540,265 A | 7/1996 | Polaschegg et al. | |
| 5,567,320 A * | 10/1996 | Goux et al. | 210/739 |
| 5,570,716 A | 11/1996 | Kamen et al. | |
| 5,572,992 A | 11/1996 | Kankkunen et al. | |
| 5,583,948 A | 12/1996 | Shibayama | |
| 5,628,908 A | 5/1997 | Kamen et al. | |
| 5,634,896 A | 6/1997 | Bryant et al. | |
| 5,640,995 A | 6/1997 | Packard et al. | |
| 5,641,405 A | 6/1997 | Keshaviah et al. | |
| 5,641,892 A | 6/1997 | Larkins et al. | |
| 5,713,865 A | 2/1998 | Manning et al. | |
| 5,741,125 A | 4/1998 | Neftel et al. | |
| 5,755,683 A | 5/1998 | Houle et al. | |
| 5,771,914 A | 6/1998 | Ling et al. | |
| 5,772,637 A | 6/1998 | Heinzmann et al. | |
| 5,788,099 A | 8/1998 | Treu et al. | |
| 5,925,011 A | 7/1999 | Faict et al. | |
| 5,925,014 A | 7/1999 | Teeple Jr. | |
| 5,938,634 A | 8/1999 | Packard | |
| 5,989,423 A | 11/1999 | Kamen | |
| 5,997,502 A | 12/1999 | Reilly et al. | |
| 6,036,680 A | 3/2000 | Horne et al. | |
| 6,041,801 A | 3/2000 | Gray et al. | |
| 6,042,784 A | 3/2000 | Wamsiedler et al. | |
| 6,065,941 A | 5/2000 | Gray et al. | |
| 6,074,359 A | 6/2000 | Keshaviah et al. | |
| 6,118,207 A | 9/2000 | Ormerod et al. | |
| 6,126,831 A | 10/2000 | Goldau et al. | |
| 6,164,621 A | 12/2000 | Bouchard et al. | |
| 6,165,154 A | 12/2000 | Gray et al. | |
| 6,187,199 B1 | 2/2001 | Goldau | |
| 6,220,295 B1 | 4/2001 | Bouchard et al. | |
| 6,223,130 B1 | 4/2001 | Gray et al. | |
| 6,228,047 B1 | 5/2001 | Dadson | |
| 6,316,864 B1 | 11/2001 | Ormerod | |
| 6,343,614 B1 | 2/2002 | Gray et al. | |
| 6,364,857 B1 | 4/2002 | Gray et al. | |
| 6,382,923 B1 | 5/2002 | Gray | |
| 6,406,276 B1 | 6/2002 | Normand et al. | |
| 6,416,293 B1 | 7/2002 | Bouchard et al. | |
| 6,459,175 B1 | 10/2002 | Potega | |
| 6,468,424 B1 | 10/2002 | Doing et al. | |
| 6,497,676 B1 | 12/2002 | Childers et al. | |
| 6,503,062 B1 | 1/2003 | Gray et al. | |
| 6,520,747 B2 | 2/2003 | Gray et al. | |
| 6,558,343 B1 | 5/2003 | Neftel | |
| 6,592,542 B2 | 7/2003 | Childers et al. | |
| 6,595,944 B2 | 7/2003 | Balschat et al. | |
| 6,604,908 B1 | 8/2003 | Bryant et al. | |
| 6,614,008 B2 | 9/2003 | Tidrick | |
| 6,648,845 B1 | 11/2003 | Gotch et al. | |
| 6,663,359 B2 | 12/2003 | Gray | |
| 6,685,831 B2 | 2/2004 | Doing et al. | |
| 6,702,774 B1 | 3/2004 | Polaschegg | |
| 6,709,417 B1 | 3/2004 | Houle et al. | |
| 6,726,656 B2 | 4/2004 | Kamen et al. | |
| 6,746,514 B2 | 6/2004 | Bedingfield et al. | |
| 6,749,403 B2 | 6/2004 | Bryant et al. | |
| 6,764,761 B2 | 7/2004 | Eu et al. | |
| 6,808,369 B2 | 10/2004 | Gray et al. | |
| 6,814,547 B2 | 11/2004 | Childers et al. | |
| 6,860,866 B1 | 3/2005 | Graf et al. | |
| 6,869,538 B2 | 3/2005 | Yu et al. | |
| 6,911,007 B2 | 6/2005 | Nier et al. | |
| 2002/0000793 A1 | 1/2002 | Hanaki | |
| 2002/0107474 A1 | 8/2002 | Noack | |
| 2002/0147423 A1 | 10/2002 | Burbank et al. | |
| 2003/0018395 A1 | 1/2003 | Crnkovich et al. | |
| 2003/0029451 A1 | 2/2003 | Blair et al. | |
| 2003/0085621 A1 | 5/2003 | Potega | |
| 2003/0111457 A1 | 6/2003 | Tidrick | |
| 2003/0130606 A1 | 7/2003 | Tuck | |
| 2003/0136189 A1 | 7/2003 | Lauman et al. | |
| 2003/0200812 A1 | 10/2003 | Kuhn et al. | |
| 2003/0204162 A1 | 10/2003 | Childers et al. | |
| 2003/0217957 A1 | 11/2003 | Bowman et al. | |
| 2003/0217961 A1 | 11/2003 | Hopping | |
| 2003/0217975 A1 | 11/2003 | Yu et al. | |
| 2003/0218623 A1 | 11/2003 | Krensky et al. | |
| 2003/0220599 A1 | 11/2003 | Lundtveit et al. | |
| 2003/0220605 A1 | 11/2003 | Bowman et al. | |
| 2003/0220607 A1 | 11/2003 | Busby et al. | |
| 2003/0220608 A1 | 11/2003 | Huitt et al. | |
| 2003/0220609 A1 | 11/2003 | Childers et al. | |
| 2003/0220627 A1 | 11/2003 | Distler et al. | |
| 2004/0010223 A1 | 1/2004 | Busby et al. | |
| 2004/0019313 A1 | 1/2004 | Childers et al. | |
| 2004/0019320 A1 | 1/2004 | Childers et al. | |
| 2004/0031756 A1 | 2/2004 | Suzuki et al. | |
| 2004/0064080 A1 | 4/2004 | Cruz et al. | |
| 2004/0067161 A1 | 4/2004 | Axelsson | |
| 2004/0082903 A1 | 4/2004 | Micheli | |
| 2004/0122353 A1 | 6/2004 | Shahmirian et al. | |
| 2004/0135078 A1 | 7/2004 | Mandro et al. | |
| 2004/0195190 A1 | 10/2004 | Min et al. | |
| 2005/0151422 A1 | 7/2005 | Gilmour | |
| 2005/0230292 A1 | 10/2005 | Beden et al. | |
| 2005/0234381 A1 | 10/2005 | Niemetzer et al. | |
| 2005/0242034 A1 | 11/2005 | Connell et al. | |
| 2006/0195064 A1 | 8/2006 | Plahey et al. | |

FOREIGN PATENT DOCUMENTS

| | | |
|---|---|---|
| EP | 1277485 | 11/2006 |
| WO | WO 92/11046 | 7/1992 |
| WO | WO 96/25214 | 8/1996 |

OTHER PUBLICATIONS

Gambro®, "DEHP-free cartridge blood sets," © Nov. 2004, Gambro, Inc., Lakewood, CO, 4 pp.

Impact of sodium and ultrafiltration profiling on haemodialysis-related hypotension, NDT Advance Access published online on Sep. 5, 2006, Yi Lun Zhou, Hui Lan Liu, Xiao Feng Duan, Ying Yao, Yi Sun, and Qun Liu.

Kidney International, vol. 66 (2004), pp. 1232-1238, Clinical consequences of an individualized dialysate sodium prescription in hemodialysis patients, Flavio M. DePaula, Aldo J. Peixoto, Luciano V. Pinto, David Dorigo, Pedro J.M. Patricio, and Sergrio F.F. Santos.

Kidney International, vol. 66, Supplement 89 (2004), pp. S1-S22, Mechanisms determining the ratio of conductivity clearance to urea clearance, Frank A. Gotch, Froilan M. Panlilio, Rosemary A. Buyaki, Erjun X. Wang, Thomas I Folden, and Nathan W. Levin.

Sleep Safe™ Operating Instructions, Fresenius Medical Care, Aug. 2000.

U.S. Appl. No. 29/224,370, filed Feb. 28, 2005, and entitled "Peritoneal Dialysis Cycler".

U.S. Appl. No. 29/224,371, filed Feb. 28, 2005, and entitled "Cassette for Peritoneal Dialysis Cycler".

U.S. Appl. No. 29/224,375, filed Feb. 28, 2005, and entitled "Peritoneal Dialysis Cycler".

De Paula et al., "*Clinical consequences of an individualized dialysate sodium prescription in hemodialysis patients*," Kidney International, vol. 66 (2004), pp. 1232-1238.

Gotch et al., "*Mechanisms determining the ratio of conductivity clearance to urea clearance*," Kidney International, vol. 66, Supplement 89 (2004), pp. S1-S22.

International Search Report and Written Opinion; PCT/US2008/064932; mailed Oct. 22, 2008.

* cited by examiner

SOLUTIONS, DIALYSATES, AND RELATED METHODS

CROSS-REFERENCE TO RELATED APPLICATIONS

This application claims the benefit of U.S. Provisional Application No. 60/940,531, filed on May 29, 2007, which is incorporated by reference herein.

TECHNICAL FIELD

This disclosure relates to solutions, dialysates, and related methods.

BACKGROUND

During hemodialysis, impurities and toxins are removed from the blood of a patient by drawing the blood out of the patient through a blood access site, typically via a catheter, and then passing the blood through an artificial kidney (often referred to as a "dialyzer"). The artificial kidney includes a semi-permeable membrane that separates a first conduit from a second conduit. Generally, a dialysis solution (often referred to as a "dialysate") is flowed through the first conduit of the dialyzer while the patient's blood is flowed through the second conduit of the dialyzer, causing impurities and toxins to be transferred from the blood to the dialysate through the semi-permeable membrane. The impurities and toxins can, for example, be removed from the blood by a diffusion process. After passing through the dialyzer, the purified blood is then returned to the patient.

SUMMARY

In one aspect of the invention, a method of performing dialysis includes placing a solution in communication with blood of a subject, where a concentration of at least one electrically conductive solute in the solution, prior to being placed in communication with the blood of the subject, is substantially equal to a concentration of the at least one electrically conductive solute in the blood of the subject.

In another aspect of the invention, a method of performing dialysis includes measuring an electrical conductivity of a solution in communication with the blood of a subject. A concentration of at least one electrically conductive solute in the solution is substantially equal to a concentration of the at least one electrically conductive solute in the blood of the subject. The method further includes determining a sodium concentration of the blood of the subject as a function of the measured electrical conductivity of the solution and placing a dialysate in communication with the blood of the subject. The dialysate, prior to being placed in communication with the blood of the subject, has a sodium concentration that is substantially equal to the determined sodium concentration of the blood of the subject.

In an additional aspect of the invention, a method includes preparing a solution for determining a sodium concentration in blood of a subject. The solution has a level of one or more electrically conductive solutes, other than sodium, that is substantially equal to a determined average level of the one or more electrically conductive solutes in blood of a population of subjects.

In another aspect of the invention, a solution for determining a sodium concentration in blood of a subject includes a concentration of multiple electrically conductive solutes that is substantially equal to a predetermined concentration of the multiple electrically conductive solutes in the blood.

In an additional aspect of the invention, a method of preparing a dialysate includes measuring an electrical conductivity of a dialysate concentrate and combining an amount of the dialysate concentrate with an amount of a liquid. The amounts of the dialysate concentrate and the liquid are determined as a function of the measured electrical conductivity of the dialysate concentrate.

In another aspect of the invention, a method of performing dialysis includes placing a test solution in communication with a dialysis patient's blood across a semi-permeable membrane for sufficient time to cause sodium ions from the patient's blood to migrate across the membrane into the test solution. The test solution, prior to being placed in communication with the patient's blood, includes concentrations of conductive solutes approximately matching expected concentrations of corresponding conductive solutes in the patient's blood and has a sodium concentration that is lower than an expected sodium concentration of the patient's blood. The method further includes measuring conductivity of the test solution both before and after the test solution is placed in communication with the patient's blood and estimating a current concentration of sodium in the patient's blood as a function of a differential between the conductivity of the test solution before being placed in communication with the patient's blood and the conductivity of the test solution after being placed in communication with the patient's blood. The method also includes providing a dialysate having a sodium concentration substantially equal to the estimated current sodium concentration in the patient's blood and placing the dialysate in communication with the patient's blood across the semi-permeable membrane to perform a dialysis treatment on the patient's blood without substantially altering the sodium concentration of the patient's blood during the performance of the dialysis treatment.

Implementations can include one or more of the following features.

In some implementations, placing the solution in communication with the blood of the subject includes passing the solution through a dialyzer.

In certain implementations, the at least one electrically conductive solute includes phosphate, sulfate, bicarbonate, potassium, calcium, and/or magnesium.

In some implementations, the method further includes, after placing the solution in communication with the blood of the subject, measuring a conductivity of the solution and determining a concentration of sodium in the blood of the subject as a function of the measured conductivity of the solution.

In certain implementations, the method further includes placing a dialysate in communication with blood of the subject. The dialysate has a concentration of sodium that is substantially equal to the determined concentration of sodium in the blood.

In some implementations, placing the dialysate in communication with the blood of the subject includes passing the dialysate through a dialyzer.

In certain implementations, the method further includes determining a dialysance of the dialyzer.

In some implementations, the sodium concentration of the dialysate differs from the determined sodium concentration of the blood by no more than a predetermined amount and/or a predetermined percentage (e.g., no more than about five percent and/or about 7.0 mEq/L, no more than about one percent and/or about 1.5 mEq/L) of the determined sodium concentration.

In certain implementations, the method further includes preparing the dialysate by combining a dialysate concentrate with water.

In some implementations, placing the dialysate in communication with the blood of the subject includes passing the dialysate through a dialyzer.

In certain implementations, the method includes passing the solution through the dialyzer prior to passing the dialysate through the dialyzer.

In some implementations, the solution is passed through the dialyzer for substantially less time than the dialysate is passed through the dialyzer.

In certain implementations, the solution is passed through the dialyzer for about five minutes or less.

In some implementations, a sodium concentration in the blood of the subject, after passing the dialysate through the dialyzer for a predetermined period of time, differs from the determined sodium concentration of the blood of the subject by no more than a predetermined amount and/or a predetermined percentage (e.g., no more than about five percent and/or about 7.0 mEq/L, no more than about one percent and/or about 1.5 mEq/L) of the determined sodium concentration of the blood of the subject.

In certain implementations, the method further includes determining a dialysance of the dialyzer as a function of the measured electrical conductivity of the solution.

In some implementations, the method further includes measuring first electrical conductivities of the solution at an inlet and an outlet of the dialyzer, and then increasing a concentration of the solution and measuring second electrical conductivities of the solution at the inlet and the outlet of the dialyzer.

In certain implementations, the method further includes performing blood tests on each of the subjects to determine the average level of the one or more electrically conductive solutes in the blood of the population of subjects.

In some implementations, the population of subjects includes a population of hemodialysis patients.

In certain implementations, the plurality of electrically conductive solutes includes phosphate, sulfate, bicarbonate, potassium, calcium, and/or magnesium.

In some implementations, the solution further includes sodium.

In certain implementations, the predetermined concentration is an average determined concentration in blood of a population of subjects.

In some implementations, the method further includes determining a sodium concentration of the dialysate concentrate as a function of the measured electrical conductivity of the dialysate concentrate.

In certain implementations, a concentration of sodium in the dialysate is substantially equal to a predetermined concentration of sodium in blood of a subject.

In some implementations, the method further includes measuring conductivities of the dialysate before and after the dialysate is placed in communication with the patient's blood and adjusting the sodium concentration of the dialysate during the dialysis treatment as a function of the before and after conductivities of the dialysate in order to substantially maintain the same sodium level in the patient's blood throughout the dialysis treatment.

In certain implementations, the method further includes preparing the test solution.

In some implementations, preparing the test solution includes determining average levels of conductive solutes in blood of a population of subjects and preparing the test solution to have levels of conductive solutes that substantially match the average levels of conductive solutes in the blood of the population of subjects.

In certain implementations, the method further includes preparing the dialysate.

In some implementations, preparing the dialysate includes determining an actual concentration of a dialysate concentrate, and combining the dialysate concentrate with an amount of water that is determined as a function of the actual concentration of the dialysate concentrate.

In certain implementations, the actual concentration of the dialysate concentrate is determined as a function of a measured conductivity of the dialysate concentrate.

Implementations can include one or more of the following advantages.

In some implementations, the concentration of the one or more electrically conductive solutes in the solution (e.g., the conductivity-testing solution) is selected to be substantially equal to the concentration of the one or more electrically conductive solutes in the subject's blood. This can help to improve the accuracy with which the sodium concentration of the blood is determined. The sodium concentration of the blood can be determined as a function of the conductivity of the solution, and the presence of differing concentrations of electrically conductive solutes in the solution and in the patient's blood can degrade the accuracy of this measurement technique. Maintaining an approximate equilibrium between the blood and the solution with respect to the one or more electrically conductive solutes can help to negate the effect of those electrically conductive solutes on the conductivity measurement, which can help to ensure that the conductivity measurement is more closely correlated with the actual concentration of sodium in the blood.

In certain implementations, the sodium concentration of the dialysate is selected to be substantially equal to the sodium concentration of the subject's blood. This can help to ensure that the sodium concentration of the blood remains substantially constant throughout the dialysis (e.g., the hemodialysis). Maintaining the sodium level of the blood at a substantially constant concentration throughout the treatment can help to reduce or prevent discomfort experienced by the subject as a result of the treatment.

In some implementations, the actual concentration (e.g., the actual sodium concentration) of the dialysate concentrate is determined and compared to the labeled concentration of the dialysate concentrate, and then the dialysate is prepared (e.g., by mixing the dialysate concentrate with water) based on the actual concentration of the dialysate concentrate, rather than the labeled concentration of the dialysate concentrate. Determining the actual concentration of the dialysate concentrate can, for example, help the preparer of the dialysate to more accurately determine desired amounts of the concentrate and another liquid (e.g., water) to combine to form the dialysate. The use of dialysates prepared in such a manner can help to maintain the sodium concentration in the subject's blood at a substantially constant level during treatment, which, as discussed above, can help to reduce or prevent discomfort experienced by the subject as a result of the treatment.

Other aspects, features, and advantages will be apparent from the description, drawings, and claims.

DETAILED DESCRIPTION

In general, this disclosure relates to solutions (e.g., conductivity-testing solutions) having a concentration of one or more electrically conductive solutes (e.g., phosphate, sulfate, bicarbonate, potassium, calcium, and/or magnesium) that is substantially equal to a concentration of those one or more electrically conductive solutes in the blood of a subject (e.g., a dialysis patient). Methods include passing the solution through a dialysate/solution conduit of a dialyzer while passing blood through a blood conduit of the dialyzer and measuring the conductivity of the solution (e.g., measuring a conductivity differential of the solution across the dialyzer). The concentration of sodium in the blood of the subject is then determined as a function of the measured conductivity (e.g., as a function of the measured conductivity differential across the dialyzer). The determined concentration of sodium in the subject's blood can be used as a model or can be taken into account to prepare a dialysate to be used to perform hemodialysis on the subject. The dialysate can, for example, be prepared to have a sodium concentration that is substantially equal to the determined sodium concentration of the subject's blood. As a result, the level of sodium in the subject's blood can be maintained at a substantially constant level throughout the blood treatment.

Figure 1:
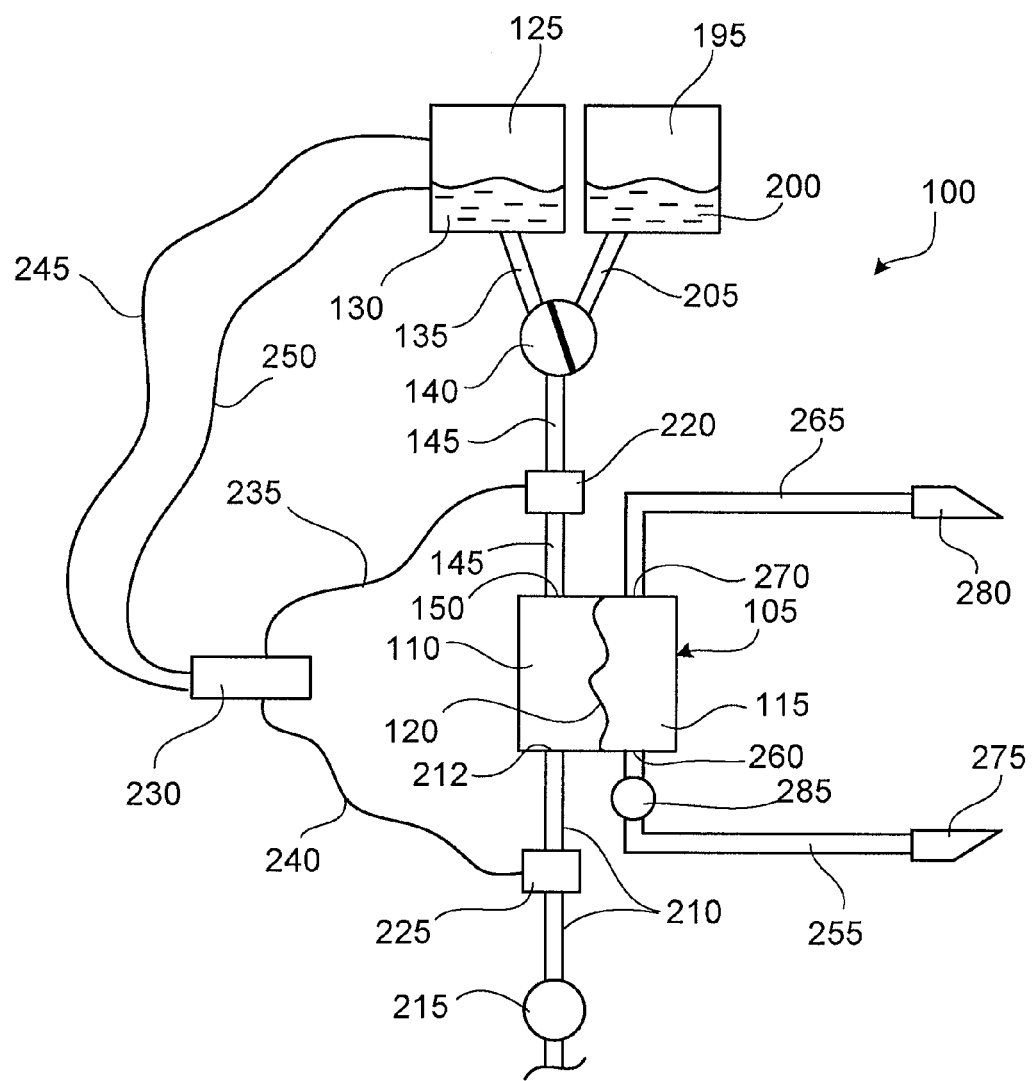
FIG. 1 is a schematic diagram of a hemodialysis apparatus.

Referring to FIG. 1, a dialysis apparatus 100 includes a dialyzer 105 that can be used to filter or purify blood. Dialyzer 105 includes a dialysate/solution conduit 110 separated from a blood conduit 115 by a semi-permeable membrane 120. Semi-permeable membrane 120 is permeable to certain impurities and toxins commonly found in uremic blood, such as phosphate, sulfate, bicarbonate, potassium, urea, creatinine, low molecular weight proteins, and other byproducts of metabolism. Semi-permeable membrane 120 is substantially impermeable to certain other blood components, such as high molecular weight proteins. Semi-permeable membrane can, for example, include (e.g., be formed of) one or more porous materials, such as a porous polysulfone. During hemodialysis, as described below, a patient's blood flows through blood conduit 115 and a dialysate 130 flows through dialysate/solution conduit 110, causing solutes to pass across membrane 120 from the blood to the dialysate and vice versa.

A dialysate supply device 125 containing dialysate 130 is in fluid communication with dialyzer 105. A dialysate supply line 135 is connected at a first end to dialysate supply device 125 and at a second end to a valve 140. Valve 140 can be arranged in a first position (shown in FIG. 1) in which dialysate 130 is permitted to flow therethrough, and in a second position in which dialysate 130 is prevented from flowing therethrough. Valve 140 can be any of various different types of valves, such as electronically controlled solenoid valves, hydraulically controlled solenoid valves, pinch valves, etc. A dialysate/solution inlet line 145 is fluidly connected to valve 105 at one end and to a dialyzer inlet opening 150 of dialyzer 105 at an opposite end. During use of apparatus 100, dialysate 130 can be transported from dialysate supply device 125 to dialyzer 105 via lines 135, 145.

Figure 2:
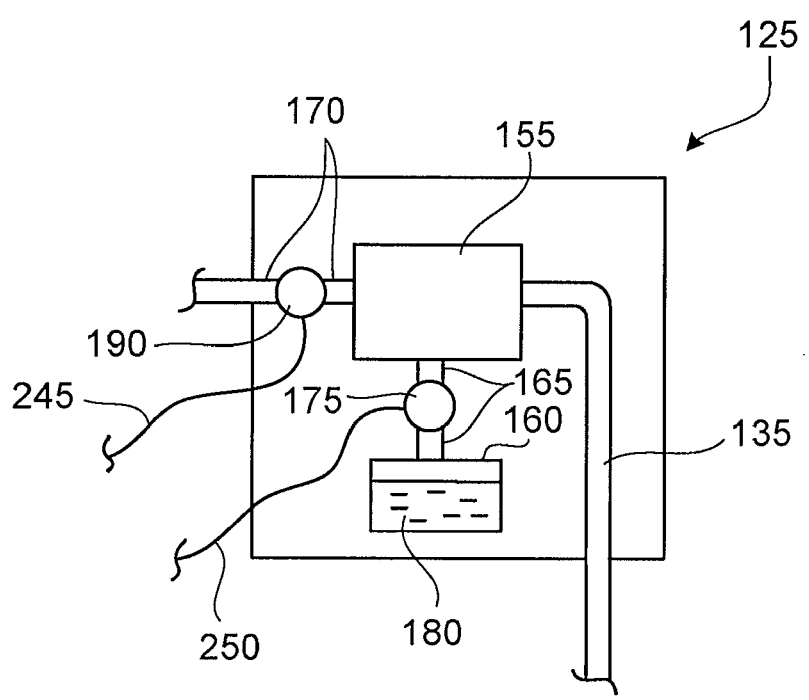
FIG. 2 is a more detailed diagram of a dialysate supply device of the dialysis apparatus of FIG. 1.

As shown in FIG. 2, dialysate supply device 125 includes a mixer 155 that is fluidly connected to a concentrate supply tank 160 via a concentrate supply line 165. A metering pump 175 is disposed within concentrate supply line 165 to enable a controllable amount of dialysate concentrate 180 to be pumped from concentrate supply tank 160 into mixer 155. Mixer 155 is also fluidly connected to a water supply source (not shown) via a water supply line 170. Water supply line 170 is equipped with a valve (e.g., a solenoid valve) 190 in order to allow the flow of water into mixer 155 to be regulated. Concentrate 180 and water can be delivered to mixer 155 and mixed together therein to form dialysate 130. Pump 175 and valve 190 can be used to control the proportions of concentrate and water used to make the dialysate.

Referring again to FIG. 1, a solution supply device 195, which contains a conductivity-testing solution 200, is in fluid communication with dialyzer 105. Solution supply device 195 is a container (e.g., a tank) that is at least partially filled with conductivity-testing solution 200. A solution supply line 205 is connected at a first end to solution supply device 195 and at a second end to valve 140. When valve 140 is arranged in the first position (shown in FIG. 1), conductivity-testing solution 200 is prevented from flowing therethrough, and when valve 140 is arranged in the second position, conductivity-testing solution 200 is permitted to flow therethrough. During use of apparatus 100, conductivity-testing solution 200 can be transported from solution supply device 195 to dialyzer 105 via lines 205 and 145.

A dialysate/solution outlet line 210 is connected to dialyzer 105 at a dialyzer outlet opening 145 located at the opposite end of dialysate/solution conduit 110. Dialysate/solution outlet line 210 is also connected to a pump 215. Pump 215 can be any of various different types of pumping devices that are capable of moving the dialysate and/or solution through dialyzer 105. Pump 215, when activated, can draw dialysate 130 from dialysate supply device 125 or conductivity-testing solution 200 from solution supply device 195 (depending on the position of valve 140) through dialysate/solution conduit 110 of dialyzer 105.

A first electrical conductivity detector 220 is disposed in dialysis/solution inlet line 145 between valve 140 and dialyzer 105, and a second electrical conductivity detector 225 is disposed in dialysate/solution outlet line 210 between dialyzer 105 and pump 215. Conductivity detectors 220, 225 are arranged to detect the conductivity of dialysate 130 and/or conductivity-testing solution 200 passing through dialysate/solution inlet and outlet lines 145, 210, respectively. Conductivity detectors 220, 225 can be any of various types of devices capable of measuring the conductivity of the dialysate and/or solution.

Conductivity detectors 220, 225 provide signals to a control unit (e.g., a microprocessor) 230 by lines (e.g., electrical wires) 235 and 240, respectively. Control unit 230 provides signals to valve 190 of water supply line 170 (FIG. 2) and pump 175 of concentrate supply line 165 (FIG. 2) via lines (e.g., electrical wires) 245 and 250. Thus, control unit 230 can, based on input received from conductivity detectors 220, 225, control the amount of concentrate and water transported to mixer 155, thereby controlling the proportions of concentrate and water used to prepare dialysate 130. Other arrangements are possible using conventional metering systems and/or proportioning valves. For example, a single signal could be output from controller 230 representing the desired volumetric and/or mass ratio of concentrate to water.

On the right-hand side of dialyzer 105, a blood inlet line 255 is fluidly connected to a blood inlet opening 260 of dialyzer 105, and a blood outlet line 265 is fluidly connected to a blood outlet opening 270 of dialyzer 105. Needle catheters 275 and 280 are attached to the free ends of blood inlet and outlet lines 255 and 265, respectively. During use, needle catheters 275 and 280 can be inserted into a blood access (e.g., a fistula) in a patient in order to draw blood from the patient and return the blood to the patient. Blood inlet line 255 is fluidly connected to a blood pump (e.g., a peristaltic roller pump) 285. When blood lines 255, 265 are connected to a patient and pump 285 is activated, blood is drawn from the patient and delivered to the blood side of dialyzer 105 through blood inlet line 255. After passing through blood conduit 115 of dialyzer 105, the blood is returned to the blood access of the patient via blood outlet line 265.

Blood lines 255, 265 and dialysate/solution lines 135, 145, 205, 210 can be any of various types of tubing capable of transporting blood or dialysate/solution therethrough. In some implementations, the blood lines and/or dialysate/solution lines are formed of one or more relatively compliant materials. Examples of materials from which the blood lines and/or dialysate/solution lines can be formed include polyvinylchloride (PVC), Di(2-ethylhexyl) phthalate (DEHP), and polyolefins.

Without wishing to be bound by theory, it is believed that subjects, including hemodialysis patients, have a natural or set level of sodium in their bodies, often referred to as their "set point." It is further believed that the set point of a subject tends to remain relatively constant, and that sodium levels deviating too far from the set point can cause discomfort to the subject. Maintaining hemodialysis patients' levels of sodium at or near their set point during hemodialysis would tend to alleviate or eliminate this cause of discomfort. Using a dialysate with a sodium concentration that is substantially equal to the sodium concentration in the blood of the hemodialysis patient can help to maintain the patient's blood sodium level at or near the patient's set point throughout the hemodialysis procedure. Methods of determining the sodium concentration in the blood of a hemodialysis patient and methods of preparing and using a dialysate having a sodium concentration that is substantially equal to the sodium concentration of the blood of the hemodialysis patient are described below.

Figure 3:
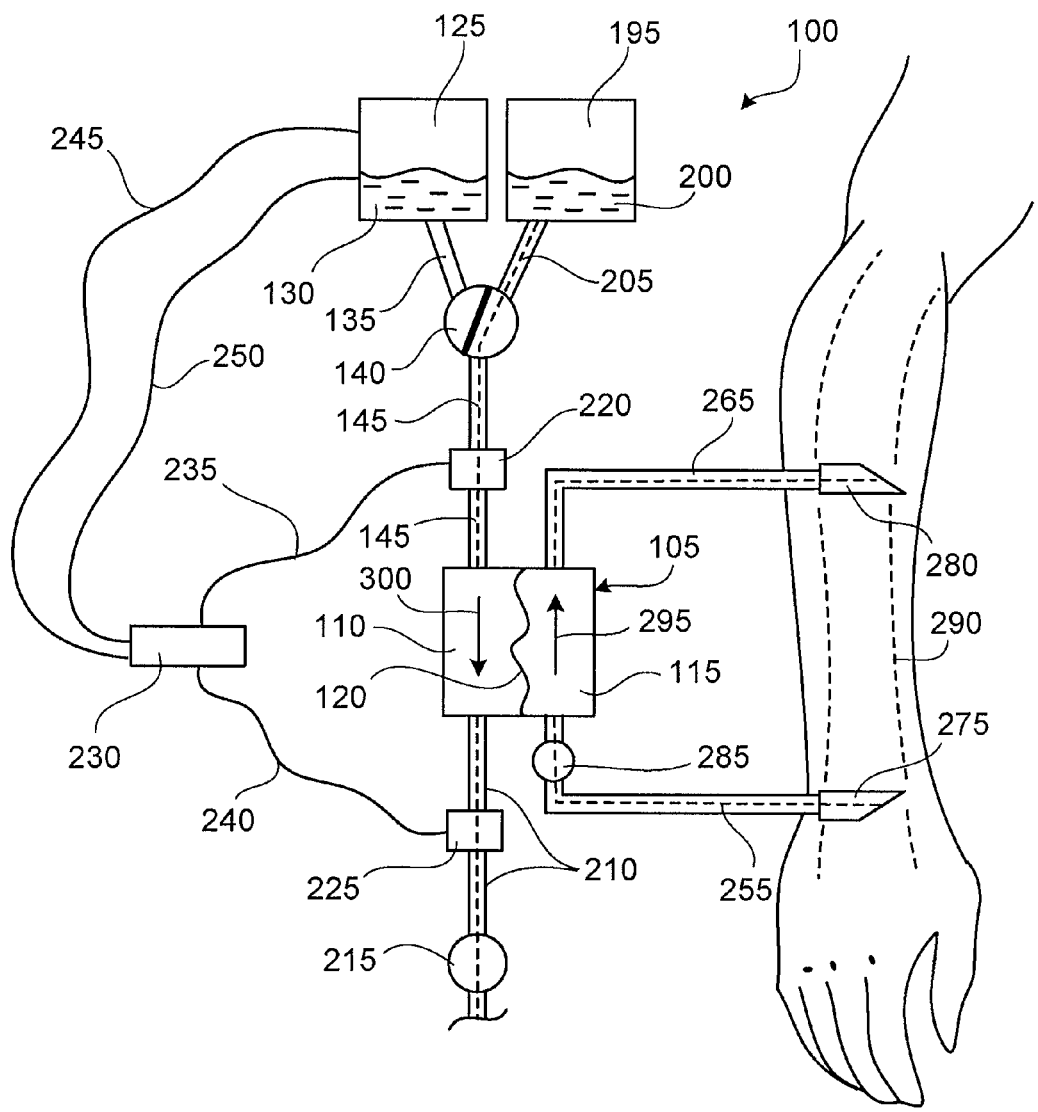
FIG. 3 is a schematic diagram illustrating a method of determining a concentration of sodium in blood of a subject using the apparatus of FIG. 1 in measurement mode.

FIG. 3 illustrates a method of determining a sodium concentration in a patient's blood using dialysis apparatus 100. Referring to FIG. 3, blood lines 255, 265 are connected to a blood access (e.g., a fistula) 290 of a patient by inserting needle catheters 275, 280 into blood access 290. After connecting blood lines 255, 265 to blood access 290, blood pump 285 is activated, causing blood to flow through blood conduit 115 of dialyzer 105 in the direction indicated by arrow 295. While flowing the blood through blood conduit 115 of dialyzer 105, conductivity-testing solution 200 is flowed in the opposite direction (i.e., in the direction of arrow 300) through dialysate/solution conduit 110 of dialyzer 105. Valve 140 can, for example, be arranged in its second position in which substantially only conductivity-testing solution 200 (and not dialysate 130) is permitted to flow into dialyzer 105. Conductivity-testing solution 200 is generally flowed through dialyzer 105 for about five minutes or less (e.g., about three minutes to about five minutes). While flowing conductivity-testing solution 200 through dialyzer 105, detectors 220, 225 measure the conductivity of conductivity-testing solution 200 as the solution enters and exits dialyzer 105.

Conductivity-testing solution 200 is formulated such that electrically conductive solutes other than sodium in the patient's blood have little or no effect on the conductivity measurements of conductivity-testing solution 200 (e.g., on the differential of conductivity of conductivity-testing solution 200 across dialyzer 105). Conductivity-testing solution 200 can, for example, be formulated such that the concentrations of phosphate, sulfate, bicarbonate, potassium, calcium, and magnesium in conductivity-testing solution 200 closely match the concentrations of those respective solutes in the patient's blood. Thus, conductivity-testing solution 200 can estimate serum sodium concentration of the patient (based on a measured conductivity of the solution) with an increased level of accuracy.

Conductivity-testing solution 200 can include about 135 mEq/L to about 145 mEq/L of sodium, about 100 mEq/L to about 110 mEq/L of chloride, about 20 mEq/L to about 45 mEq/L of bicarbonate, and about 3.0 mEq/L to about 5.0 mEq/L of potassium, about 6.0 mg/dl to about 8.0 mg/dl of phosphate, and about 6.0 mg/dl to about 8.0 mg/dl of sulfate. In some implementations, solution 200 includes about 140 mEq/L of sodium, about 100 mEq/L of chloride, about 20 mEq/L of bicarbonate, about 4.0 mEq/L of potassium, about 7.0 mg/dl of phosphates, and about 7.0 mg/dl of sulfates.

Various techniques can be used to determine and prepare a desirable composition of conductivity-testing solution 200. For example, to prepare conductivity-testing solution 200, a large sample of dialysis patients can be tested to determine an average level of the above-noted electrically conductive solutes in their blood. Conductivity-testing solution 200 can then be formulated to include similar (e.g., identical) levels of those solutes. By using the average level of blood solute concentrations in a targeted population of subjects, relatively accurate predictions of other hemodialysis patients' blood levels can be predicted without having to use more invasive and/or time-consuming procedures, such as drawing and testing the blood of each patient undergoing treatment. In addition, because conductivity-testing solution 200 need not be specifically tailored for each individual patient, the solution can be manufactured and distributed in large batches, and can thus be manufactured relatively inexpensively.

Due to the closely matched concentrations of electrically conductive solutes, such as phosphate, sulfate, bicarbonate, potassium, calcium, and magnesium, in conductivity-testing solution 200 and in the patient's blood, little if any diffusion of those electrically conductive solutes occurs across membrane 120. Consequently, the conductivity measurements of conductivity-testing solution 200, as measured by detectors 220, 225, can be more closely correlated with the level of sodium in the patient's blood. Therefore, as compared to traditional dialysate solutions, conductivity-testing solution 200 can be used to more accurately determine the level of sodium in the patient's blood as a function of the conductivity (e.g., change in conductivity across dialyzer 105) of the conductivity-testing solution.

After determining the conductivity of conductivity-testing solution 200 at detectors 220 and 225, the conductivity values are transferred from detectors 220, 225 to control unit 230. Control unit 230 then determines (e.g., calculates) the level of sodium in the patient's blood as a function of the measured conductivity values. The level of sodium in the patient's blood can, for example, be determined using the following equation:

$$Cb_i = Cd_i[((D(1-Q_f/Q_e)-Qd(1-Cnd_o/Cnd_i)+Qf(Cnd_o/Cnd_i))/(D(1-Q_f/Q_e)+Q_f)] \quad (1)$$

In equation (1) above, $Cd_i$ is the base sodium concentration of the conductivity-testing solution; $Q_f$ is the ultrafiltration rate; $Q_e$ is the blood water flow rate which can be approximated as 0.85 Qb; D is the conductivity dialysance; and $Cnd_o$, $Cnd_i$ are the conductivies of the conductivity testing solution in the outlet and inlet streams, respectively.

As an alternative to or in addition to calculating the level of sodium in the patient's blood, control unit 230 can use a look-up table that includes multiple conductivity values (e.g., multiple differential of conductivity values) and corresponding blood sodium concentrations. In some implementations, the look-up table is used as a quality control mechanism to compare a calculated blood sodium level to a predetermined theoretical blood sodium level. In such implementations, if the calculated blood sodium level differs from the theoretical blood sodium level by greater than a predetermined acceptable amount, an indicator (e.g., an audio and/or visual indicator) can be activated to notify the user of the disparity.

After determining the concentration of sodium in the patient's blood, dialysate 130 can be prepared to include a concentration of sodium that is substantially equal to the concentration of sodium determined to exist in the patient's blood. Dialysate 130 can, for example, be prepared to have a sodium concentration that differs from the sodium concentration in the subject's blood by no more than about five percent (e.g., no more than about one percent) and/or no more than about 7.0 mEq/L (e.g. no more than about 1.5 mEq/L). Referring to FIGS. 2 and 3, to formulate dialysate 130 such that it has a sodium concentration substantially equal to that of the patient's blood, the proportion of dialysate concentrate to water can be altered by control unit 230. Control unit 230, which is in electrical communication with pump 175 of concentrate supply line 165 and valve 190 of water supply line 170 can operate pump 175 and valve 190 to deliver desired proportions of dialysate concentrate and water to mixer 155 of dialysate supply device 125. The sodium level of the dialysate can, for example, be increased or decreased, by altering the proportions of dialysate concentrate and water. The levels of other solutes within the dialysate concentrate will be increased or decreased along with the sodium when the proportions of dialysate concentrate and water are changed. However, it is believed that, due to the relatively small amounts of those other solutes in the dialysate, the increased or decreased levels of those other solutes will have a negligible effect on the treatment of the patient's blood.

Figure 4:
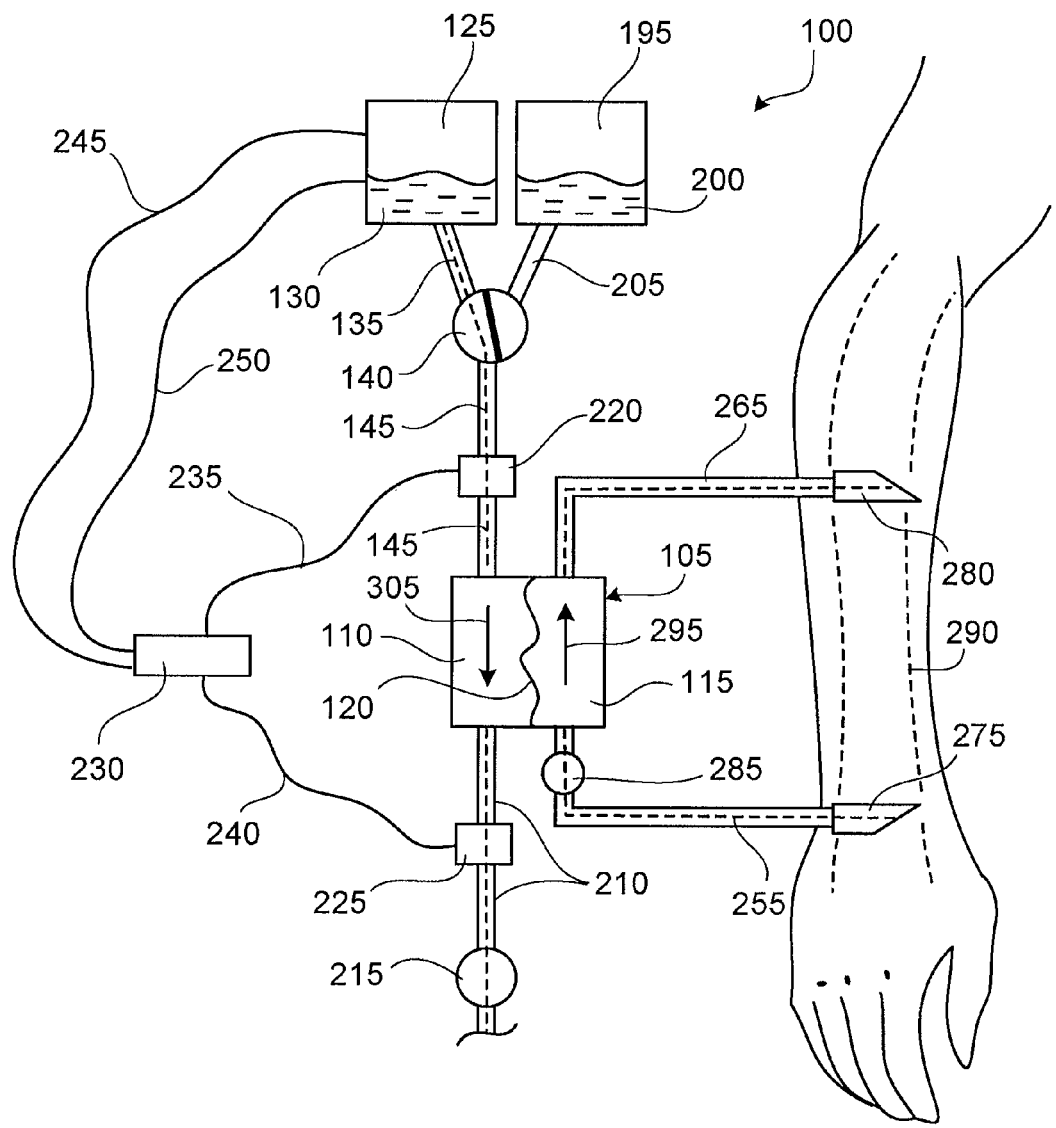
FIG. 4 is a schematic diagram illustrating a method of treating blood of a subject using the apparatus of FIG. 1 in treatment mode.

After preparing dialysate 130, hemodialysis can be performed using dialysate 130 in order to remove impurities and toxins as well as excess water and sodium from the blood of the patient. Referring to FIG. 4, to perform hemodialysis, blood lines 255, 265 are connected (e.g., remain connected) to blood access 290 of the patient, and pump 285 is activated (e.g., remains activated) such that the patient's blood is caused to flow through blood conduit 115 of dialyzer 105 in the direction indicated by arrow 295. While flowing the patient's blood through blood conduit 115 of dialyzer 105, dialysate 130 is pumped through dialysate/solution conduit 110 of dialyzer 105 in a direction opposite to that of the blood (i.e., the direction indicated by arrow 305).

Due to the differing compositions of dialysate 130 and the patient's blood, certain impurities and toxins, such as phosphate, sulfate, bicarbonate, potassium, calcium, and magnesium, are diffused through membrane 120 of dialyzer 105, from the blood into the dialysate or vice versa. Other impurities, such as urea and creatinine, can similarly be diffused across membrane 120. Dialysate 130, for example, generally has concentrations of phosphate, sulfate, potassium, calcium, and magnesium that are lower than the concentrations of phosphate, sulfate, potassium, calcium, and magnesium, respectively, found in blood 220, and dialysate 130 generally has a concentration of bicarbonate that is higher than the concentration of bicarbonate in blood 220. As a result, phosphate, sulfate, potassium, calcium, and magnesium will generally diffuse from blood 220 into dialysate 130 during treatment while bicarbonate will generally diffuse from dialysate 130 into blood 220 during treatment. Typical concentrations within dialysate 130 are about 140 mEq/L of sodium, about 100 mEq/L of chloride, about 35-40 mEq/L of bicarbonate, about 2.0 mEq/L of potassium, 2.5 mEq/L of calcium, 2.0 mEq/L of magnesium and no phosphate or sulfate. However, as discussed above, the sodium concentration in dialysate 130 will vary depending on the sodium level in the blood of the particular patient being treated. The other components of dialysate 130 can also vary depending on, among other things, the type of treatment to be performed.

In addition to the above-described diffusion technique, an ultrafiltration process is used to remove certain components, such as water, from the blood by convection. To remove components from the blood using ultrafiltration, a pressure gradient is produced between dialysate/solution conduit 110 and blood conduit 115. Due to the pressure gradient across membrane 120, water and certain solutes contained therein, such as sodium, pass across membrane 120 from the blood to dialysate 130 during treatment.

Due to the substantially equal levels of sodium in the blood and the dialysate, after passing the dialysate and blood through dialyzer 105 for a desired period of time (e.g., about 150 minutes to about 210 minutes), the sodium concentration in the blood will differ from the predicted sodium concentration of the blood by no more than about five percent (e.g., by no more than about one percent) of the predicted sodium concentration of the blood and/or by no more than about 7.0 mEq/L (e.g., by no more than about 1.5 mEq/L).

After purifying the blood and removing the excess liquid and sodium from the blood, the treated blood is returned to the patient via blood outlet line 265 and the spent dialysate is transferred to a waste drain.

While certain implementations have been described above, other implementations are possible.

While implementations above describe predicting a patient's blood sodium concentration based on an average level of sodium found in a previously tested group of hemodialysis patients, the levels of electrically conductive solutes in a patient's blood can alternatively or additionally be determined on an individual basis by, for example, drawing blood from the patient prior to his/her treatment and testing the levels of the electrically conductive solutes in the blood. A conductivity-testing solution having levels of electrically conductive solutes substantially equal to those found in the patient's blood can then be produced and used in a process similar to those described above to determine the level of sodium in the patient's blood. For example, the concentrations of phosphate, sulfate, bicarbonate, potassium, calcium, and magnesium in the conductivity-testing solution can be approximately matched to the patient's plasma solute concentrations at the beginning of dialysis.

In some implementations, using pre-packaged dialysate concentrate 180, the sodium concentration of dialysate concentrate 180 is tested prior to formulating dialysate 130 even though the label indicates that the concentrate has a particular concentration. In such implementations, the proportions of water and concentrate 180 used to form dialysate 130 can be adjusted prior to hemodialysis if it is determined that the actual sodium concentration of the dialysate concentrate differs from the labeled concentration (e.g., the concentration provided by the manufacturer of the concentrate). To test the sodium concentration of dialysate concentrate 180, the dialysate concentrate is flowed through dialysate/solution conduit 110 of dialyzer 105, and the conductivity of the dialysate concentrate is measured by one or both of detectors 220, 225. A technique similar to that described above with respect to the delivery of dialysate 130 to dialyzer 105 can be used to deliver dialysate concentrate 180 to dialyzer 105. However, rather than supplying both water and concentrate to mixer 155 (FIG. 2), the concentrate alone is delivered to mixer 155. While flowing dialysate concentrate 180 through dialysate/solution conduit 110 of dialyzer 105, the blood of the patient is prevented from passing through blood conduit 115 of dialyzer 105. Blood lines 255, 265 can, for example, be disconnected from the patient prior to flowing dialysate concentrate 180 through dialyzer 105. Blood lines 255, 265 can alternatively or additionally include shut-off valve or a bypass valve to prevent the blood from passing through the dialyzer. By preventing the blood from flowing through dialyzer 105, diffusion and/or convection of blood components or solutes into dialysate concentrate 180 through membrane 120 of dialyzer 105 can be prevented. Consequently, the true composition of the dialysate can be tested.

After measuring the conductivity of the concentrate, the conductivity values are communicated (e.g., electronically transferred) to control unit 230. Control unit 230 can then determine the sodium concentration of dialysate concentrate 180. While dialysate concentrate 180 includes certain electrically conductive solutes (e.g., bicarbonate, potassium, calcium, and/or magnesium) in addition to sodium, the relative amount of those electrically conductive solutes, as compared to the sodium, remains very small throughout the testing process. This is due, at least in part, to the fact that electrically conductive solutes are not transferred from the blood to the dialysate concentrate during the testing process. Due to the relatively small amount of those electrically conductive solutes in dialysate concentrate 180, it is believed that the effect of those solutes on the measured conductivity and the determination of sodium concentration of the dialysate concentrate will be negligible.

After determining the actual concentration of sodium in dialysate concentrate 180, control unit 230 determines whether the difference (if any) between the determined sodium concentration and the labeled sodium concentration warrants an adjustment to the proportions of water and concentrate used to prepare dialysate 130. If, for example, the sodium concentration determined by control unit 230 differs from the labeled concentration by more than about one percent (e.g., by more than about 0.5 percent) of the labeled concentration and/or by more than about 1.5 mEq/L (e.g., by more than about 1.0 mEq/L), then the proportions of the concentrate and water used to form dialysate 130 can be altered to compensate for the erroneous labeled concentration. Adjusting the proportions of the concentrate and water used to form dialysate 130 can help to ensure that dialysate 130 has sodium concentration that is substantially equal to the sodium concentration of the blood to be treated.

While the implementations above describe the use of a dialysate concentrate (e.g., the use of a dialysate concentrate mixed with varying amounts of water) to form dialysate 130, other techniques can alternatively or additionally be used. In some implementations, for example, one or more of the individual components found in the dialysate concentrate are separately combined with water to form the dialysate. As a result, the concentration of one component, such as sodium, can be altered without altering the concentrations of other components of the dialysate, such as bicarbonate, potassium, calcium, and magnesium. In such implementations, as an alternative to or in addition to concentrate supply tank 160 (FIG. 2), multiple different concentrate or concentrate component supply tanks can be fluidly connected to mixer 155 of dialysate supply device 125 to enable the concentrate or concentrate components to be added to mixer 155 when forming the dialysate.

While implementations above describe preparing the dialysate by mixing dialysate concentrate or concentrate components with water, the user can alternatively or additionally select the dialysate from a variety of premixed dialysates of different concentrations. To treat a patient, the treatment provider can select and use the premixed dialysate having a sodium concentration that most closely matches the sodium concentration of the patient's blood. In such implementations, the dialysate supply device could merely be a container (e.g., a tank) that contains the premixed dialysate.

In some implementations, dialysis apparatus 100 also includes temperature detectors (not shown) positioned proximate to detectors 220, 225. The temperature detectors can be configured to determine the temperature of dialysate 130 and/or conductivity-testing solution 200 flowing through dialysate/solution lines 145, 210. The temperature detectors can be in communication with control unit 230 such that the detected temperature data can be transferred to control unit 230. Control unit 230 can, for example, use the temperature readings to adjust conductivity readings and/or sodium concentration determinations that may be affected by a temperature differential in the dialysate or solution across dialyzer 105.

While detectors 220, 225 have been described as conductivity detectors, other types of detectors and/or techniques can alternatively or additionally be used to determine the sodium concentration of the blood. Examples of other types of detectors include ion selective electrodes and flame photometers.

While blood access 290 has been described as a fistula, other types of blood accesses, such as grafts, shunts, and catheters, can alternatively or additionally be used.

While solution supply device 195 has been described as a container containing a premixed solution, other types of solution supply devices can alternatively or additionally be used. In some implementations, for example, solution supply device 195 includes a solution concentrate supply and a water supply. In such implementations, the solution concentrate and water can be mixed together (e.g., in a mixing tank) to form conductivity-testing solution 200.

While the methods, solutions, and dialysates described in implementations above relate to hemodialysis, the methods, solutions, and/or dialysates can alternatively or additionally be used for other types of dialysis, such as peritoneal dialysis.

Other implementations are within the scope of the following claims.

What is claimed is:

1. A method of performing dialysis, the method comprising:
   prior to beginning dialysis treatment during which dialysate is placed in communication with blood of a subject, placing a test solution in communication with the blood of a the subject, wherein a concentration of at least one electrically conductive solute in the test solution, prior to being placed in communication with the blood of the subject, is substantially equal to a concentration of the at least one electrically conductive solute in the blood of the subject.

2. The method of claim 1, wherein placing the test solution in communication with the blood of the subject comprises passing the test solution through a dialyzer.

3. The method of claim 1, wherein the at least one electrically conductive solute comprises one or more members selected from the group consisting of phosphate, sulfate, bicarbonate, potassium, calcium, and magnesium.

4. The method of claim 1, wherein the at least one electrically conductive solute comprises phosphate, sulfate, bicarbonate, potassium, calcium, and magnesium.

5. The method of claim 1, further comprising, after placing the test solution in communication with the blood of the subject, measuring a conductivity of the test solution and determining a concentration of sodium in the blood of the subject as a function of the measured conductivity of the solution.

6. The method of claim 5, further comprising placing the dialysate in communication with the blood of the subject, the dialysate having a concentration of sodium that is substantially equal to the determined concentration of sodium in the blood.

7. The method of claim 6, wherein placing the dialysate in communication with the blood of the subject comprises passing the dialysate through a dialyzer.

8. A method of performing dialysis, the method comprising:
   prior to beginning dialysis treatment during which dialysate is placed in communication with blood of a subject, measuring an electrical conductivity of a test solution in communication with the blood of the subject, a concentration of at least one electrically conductive solute in the test solution, prior to being placed in communication with the blood of the subject, being substantially equal to a concentration of the at least one electrically conductive solute in the blood of the subject;
   determining a sodium concentration of the blood of the subject as a function of the measured electrical conductivity of the test solution; and
   placing the dialysate in communication with the blood of the subject to perform the dialysis treatment, the dialysate, prior to being placed in communication with the blood of the subject, having a sodium concentration that is substantially equal to the determined sodium concentration of the blood of the subject.

9. The method of claim 8, wherein the sodium concentration of the dialysate differs from the determined sodium concentration of the blood by no more than about five percent of the determined sodium concentration.

10. The method of claim 8, wherein the sodium concentration of the dialysate differs from the determined sodium concentration of the blood by no more than about 7.5 mEq/L.

11. The method of claim 8, further comprising preparing the dialysate by combining a dialysate concentrate with water.

12. The method of claim 8, wherein the at least one electrically conductive solute comprises one or more members selected from the group consisting of phosphate, sulfate, bicarbonate, potassium, calcium, and magnesium.

13. The method of claim 8, wherein placing the dialysate in communication with the blood of the subject comprises passing the dialysate through a dialyzer.

14. The method of claim 13, further comprising passing the test solution through the dialyzer prior to passing the dialysate through the dialyzer.

15. The method of claim 14, wherein the test solution is passed through the dialyzer for substantially less time than the dialysate is passed through the dialyzer.

16. The method of claim 15, wherein the test solution is passed through the dialyzer for about five minutes or less.

17. The method of claim 13, wherein a sodium concentration in the blood of the subject, after passing the dialysate through the dialyzer for a predetermined period of time, differs from the determined sodium concentration of the blood of the subject by no more than about five percent of the determined sodium concentration of the blood of the subject.

18. A method of performing dialysis, the method comprising:
   prior to beginning dialysis treatment during which dialysate is placed in communication with blood of a dialysis patient across a semi-permeable membrane, placing a test solution in communication with the dialysis patient's blood across the semi-permeable membrane for sufficient time to cause sodium ions from the patient's blood to migrate across the membrane into the test solution, the test solution, prior to being placed in communication with the patient's blood, comprising concentrations of conductive solutes approximately matching expected concentrations of corresponding conductive solutes in the patient's blood and having a sodium concentration that is lower than an expected sodium concentration of the patient's blood;
   measuring conductivity of the test solution both before and after the test solution is placed in communication with the patient's blood;
   estimating a current concentration of sodium in the patient's blood as a function of a differential between the conductivity of the test solution before being placed in communication with the patient's blood and the conductivity of the test solution after being placed in communication with the patient's blood;
   providing a dialysate having a sodium concentration substantially equal to the estimated current sodium concentration in the patient's blood; and
   placing the dialysate in communication with the patient's blood across the semi-permeable membrane to perform a the dialysis treatment on the patient's blood without substantially altering the sodium concentration of the patient's blood during the performance of the dialysis treatment.

19. The method of claim 18, further comprising:
   measuring conductivities of the dialysate before and after the dialysate is placed in communication with the patient's blood; and
   adjusting the sodium concentration of the dialysate during the dialysis treatment as a function of the before and after conductivities of the dialysate in order to substantially maintain the same sodium level in the patient's blood throughout the dialysis treatment.

20. The method of claim 18, further comprising preparing the test solution.

21. The method of claim 20, wherein preparing the test solution comprises determining average levels of conductive solutes in blood of a population of subjects and preparing the test solution to have levels of conductive solutes that substantially match the average levels of conductive solutes in the blood of the population of subjects.

22. The method of claim 18, further comprising preparing the dialysate.

23. The method of claim 22, wherein preparing the dialysate comprises determining an actual concentration of a dialysate concentrate, and combining the dialysate concentrate with an amount of water, the amount of water being determined as a function of the actual concentration of the dialysate concentrate.

24. The method of claim 23, wherein the actual concentration of the dialysate concentrate is determined as a function of a measured conductivity of the dialysate concentrate.

25. The method of claim 18, wherein the at least one electrically conductive solute comprises phosphate, sulfate, bicarbonate, potassium, calcium, and magnesium.

26. The method of claim 18, wherein the conductive solutes comprises phosphate, sulfate, bicarbonate, potassium, calcium, and magnesium.

\* \* \* \* \*

UNITED STATES PATENT AND TRADEMARK OFFICE
CERTIFICATE OF CORRECTION

PATENT NO. : 8,182,692 B2  
APPLICATION NO. : 12/128167  
DATED : May 22, 2012  
INVENTOR(S) : Frank A. Gotch Page 1 of 1

It is certified that error appears in the above-identified patent and that said Letters Patent is hereby corrected as shown below:

Claim 1, column 12, line 49:
delete "a the" and replace with --the--.

Claim 18, column 14, line 27:
delete "a the" and replace with --the--.

Signed and Sealed this
Twenty-fourth Day of July, 2012

David J. Kappos
*Director of the United States Patent and Trademark Office*